(12) United States Patent
Grewe et al.

(10) Patent No.: US 9,060,852 B2
(45) Date of Patent: Jun. 23, 2015

(54) METHOD FOR MAKING A FLEXIBLE STENT-GRAFT

(75) Inventors: David G. Grewe, West Lafayette, IN (US); Keith R. Milner, West Lafayette, IN (US); Blayne A. Roeder, Lafayette, IN (US); Steven J. Charlebois, West Lafayette, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 441 days.

(21) Appl. No.: 13/438,549

(22) Filed: Apr. 3, 2012

(65) Prior Publication Data

US 2012/0259170 A1 Oct. 11, 2012

Related U.S. Application Data

(60) Provisional application No. 61/473,437, filed on Apr. 8, 2011.

(51) Int. Cl.
| | | |
|---|---|---|
| A61F 2/07 | (2013.01) | |
| A61F 2/91 | (2013.01) | |
| A61F 2/915 | (2013.01) | |
| A61F 2/89 | (2013.01) | |

(52) U.S. Cl.
CPC ............ *A61F 2/07* (2013.01); *A61F 2002/072* (2013.01); *A61F 2/91* (2013.01); *A61F 2002/91566* (2013.01); *A61F 2240/001* (2013.01); *A61F 2/89* (2013.01); *A61F 2/915* (2013.01); *A61F 2002/075* (2013.01); *A61F 2220/005* (2013.01)

(58) Field of Classification Search
CPC .............................. A61F 2/07; A61F 2002/072
USPC .......... 600/36; 623/1.13, 1.15, 1.18–1.2, 1.44
See application file for complete search history.

(56) References Cited

U.S. PATENT DOCUMENTS

| | | | |
|---|---|---|---|
| 5,316,023 A | | 5/1994 | Palmaz et al. |
| 5,383,925 A | * | 1/1995 | Schmitt ........................ 623/1.53 |
| 5,723,004 A | | 3/1998 | Dereume et al. |
| 6,162,537 A | * | 12/2000 | Martin et al. .................. 428/373 |
| 6,576,009 B2 | | 6/2003 | Ryan et al. |
| 6,613,078 B1 | | 9/2003 | Barone |
| 7,377,937 B2 | | 5/2008 | Dolan |
| 7,413,575 B2 | | 8/2008 | Phaneuf et al. |
| 2003/0097170 A1 | | 5/2003 | Friedrich et al. |
| 2006/0085063 A1 | | 4/2006 | Shastri et al. |
| 2007/0269481 A1 | | 11/2007 | Li et al. |
| 2008/0195193 A1 | * | 8/2008 | Purdy et al. .................. 623/1.16 |
| 2008/0200975 A1 | * | 8/2008 | Dubson ........................ 623/1.15 |

(Continued)

FOREIGN PATENT DOCUMENTS

WO WO 97/07751 A1 3/1997

OTHER PUBLICATIONS

European Search Report for related application No. 12163495.0 filed Apr. 5, 2012; Mailed Aug. 7, 2012.

*Primary Examiner* — Charles A Marmor, II
*Assistant Examiner* — Carrie R Dorna
(74) *Attorney, Agent, or Firm* — Brinks Gilson & Lione

(57) ABSTRACT

A method of making a stent-graft is provided. The method includes mounting a stent on a mandrel so that the stent is stretched when it is on the mandrel. A graft layer is then adhered to the stent while it is mounted on the mandrel. When the stent-graft is removed from the mandrel, the stent contracts and the graft layer becomes partially wrinkled when the stent is in its expanded relaxed state.

15 Claims, 3 Drawing Sheets

(56) References Cited

U.S. PATENT DOCUMENTS

2008/0319530 A1 12/2008 Leewood et al.
2009/0248131 A1 10/2009 Greenan
2010/0280590 A1 11/2010 Sun et al.

* cited by examiner

METHOD FOR MAKING A FLEXIBLE STENT-GRAFT

This application claims priority to U.S. Provisional Application No. 61/473,437, filed Apr. 8, 2011, which is hereby incorporated by reference herein.

BACKGROUND

The present invention relates generally to medical devices and more particularly to a method of manufacturing a self-expanding stent-graft with wrinkles in the expanded relaxed state.

Stents have become relatively common devices for treating a number of organs, such as the vascular system, colon, biliary tract, urinary tract, esophagus, trachea and the like. Stents are useful in treating various ailments including blockages, occlusions, narrowing conditions and other related problems that restrict flow through a passageway (generally referred to as a stenosis). Stents are also useful in a variety of other medical procedures including treating various types of aneurysms.

For example, stents may be used to treat numerous vessels in the vascular system, including coronary arteries, peripheral arteries (e.g., carotid, brachial, renal, iliac and femoral), and other vessels. Stents have become a common alternative for treating vascular conditions because stenting procedures are considerably less invasive than other alternatives. As an example, stenoses in the coronary arteries have traditionally been treated with bypass surgery. In general, bypass surgery involves splitting the chest bone to open the chest cavity and grafting a replacement vessel onto the heart to bypass the stenosed artery. However, coronary bypass surgery is a very invasive procedure that is risky and requires a long recovery time for the patient. By contrast, stenting procedures are performed translumially and do not require open surgery. Thus, recovery time is reduced and the risks of surgery are minimized.

Many different types of stents and stenting procedures are possible. In general, however, stents are typically designed as tubular support structures that may be inserted percutaneously and translumially through a body passageway. Typically, stents are made from a structure that wraps around at least a portion of a circumference and are adapted to compress and expand between a smaller and larger diameter. Stents may be self-expanding so that they elastically expand out to the larger diameter, or may be balloon-expandable so that they require a force to expand to the larger diameter. However, other types of stents are designed to have a fixed diameter and are not generally compressible. Although stents may be made from many types of materials, including non-metallic materials and natural tissues, common examples of metallic materials that may be used to make stents include stainless steel and nitinol. Other materials may also be used, such as cobalt-chrome alloys, amorphous metals, tantalum, platinum, gold, titanium, polymers and/or compatible tissues. Typically, stents are implanted within an artery or other passageway by positioning the stent within the lumen to be treated and then expanding the stent from a compressed diameter to an expanded diameter. The ability of the stent to expand from a compressed diameter makes it possible to thread the stent through narrow, tortuous passageways to the area to be treated while the stent is in a relatively small, compressed diameter. Once the stent has been positioned and expanded at the area to be treated, the tubular support structure of the stent contacts and radially supports the inner wall of the passageway. The implanted stent may be used to mechanically prevent the passageway from closing in order to keep the passageway open to facilitate fluid flow through the passageway. Conversely, stents may also be used to support a graft layer to prevent fluid flow through the side walls of the stent. However, these are only some of the examples of how stents may be used, and stents may be used for other purposes as well.

Self-expanding stents are one common type of stent used in medical procedures. Self-expanding stents are increasingly being used by physicians because of their adaptability to a variety of different conditions and procedures. Self-expanding stents are usually made of shape memory materials or other elastic materials that act like a spring. Typical metals used in this type of stent include nitinol and 304 stainless steel. However, other materials may also be used. To facilitate stent implantation, self-expanding stents are normally installed on the end of a catheter in a low profile, compressed state. The stent is typically retained in the compressed state by inserting the stent into a sheath at the end of the catheter. The stent is then guided to the portion of the vessel to be treated. Once the catheter and stent are positioned adjacent the portion to be treated, the stent is released by pulling, or withdrawing, the sheath rearward. Normally, a step or other feature is provided on the catheter to prevent the stent from moving rearward with the sheath. After the stent is released from the retaining sheath, the stent springs radially outward to an expanded diameter until the stent contacts and presses against the vessel wall. Traditionally, self-expanding stents have been used in a number of peripheral arteries in the vascular system due to the elastic characteristic of these stents. One advantage of self-expanding stents for peripheral arteries is that traumas from external sources do not permanently deform the stent. As a result, the stent may temporarily deform during unusually harsh traumas and spring back to its expanded state once the trauma is relieved. However, self-expanding stents may be used in many other applications as well.

Stents may also be used in combination with other components to treat a number of medical conditions. For example, stent-graft assemblies are commonly used in the treatment of aneurysms. As those in the art well know, an aneurysm is an abnormal widening or ballooning of a portion of an artery. Generally, this condition is caused by a weakness in the blood vessel wall. High blood pressure and atherosclerotic disease may also contribute to the formation of aneurysms. Common types of aneurysms include aortic aneurysms, cerebral aneurysms, popliteal artery aneurysms, mesenteric artery aneurysms, and splenic artery aneurysms. However, it is also possible for aneurysms to form in blood vessels throughout the vasculature. If not treated, an aneurysm may eventually rupture, resulting in internal hemorrhaging. In many cases, the internal bleeding may be so massive that a patient can die within minutes of an aneurysm rupture. For example, in the case of aortic aneurysms, the survival rate after a rupture can be as low as 20%.

Traditionally, aneurysms have been treated with surgery. For example, in the case of an abdominal aortic aneurysm, the abdomen is surgically opened, and the widened section of the aorta is typically dissected longitudinally. A graft material, such as Dacron, is then inserted into the vessel and sutured at each end to the inner wall of the non-widened portions of the vessel. The dissected edges of the vessel may then be overlapped and sutured to enclose the graft material within the vessel. In smaller vessels where the aneurysm forms a balloon-like bulge with a narrow neck connecting the aneurysm to the vessel, the surgeon may put a clip on the blood vessel wall at the neck of the aneurysm between the aneurysm and the primary passageway of the vessel. The clip then prevents blood flow from the vessel from entering the aneurysm.

An alternative to traditional surgery is endovascular treatment of the blood vessel with a stent-graft. This alternative involves implanting a stent-graft in the blood vessel across the aneurysm using conventional catheter-based placement techniques. The stent-graft treats the aneurysm by sealing the wall of the blood vessel with a generally impermeable graft material. Thus, the aneurysm is sealed off and blood flow is kept within the primary passageway of the blood vessel. Increasingly, treatments using stent-grafts are becoming preferred since the procedure results in less trauma and a faster recuperation.

One problem that can occur with self-expanding stent-grafts is that the graft layer can become excessively tight on the stent when the stent is in its expanded relaxed state. This can be undesirable because it may overstress the graft layer and raise fatigue concerns. This may be a particular concern with stent-grafts that are implanted in passageways that are subject to a high degree of axial stretching, bending, twisting or changes in radial shape. One example of a passageway that undergoes an extreme amount of such movement is the superficial femoral artery.

Although overstretching of the graft layer may be a concern with many types of graft materials, inelastic graft materials may raise particular concerns. For example, Dacron (polyethylene terephthalate or PET) is one graft material that is commonly preferred due to its low permeability and biocompatibility. However, it is possible for Dacron to crack if excessive tensile forces are applied to the material.

Accordingly, the inventors believe a method for making a stent-graft that minimizes overstretching of the graft layer may be desirable.

SUMMARY

A method of making a stent-graft is described that results in the graft layer being partially wrinkled when the stent is in the expanded relaxed state. This may allow the stent-graft to be more flexible and to resist cracking, particularly when the graft material is made from an inelastic material. In one of the described methods, the stent is mounted on a mandrel with an outer circumference that is larger than the diameter of the stent in the expanded relaxed state. The stent may also be axially stretched on the mandrel, and may also be axially stretched more on one side of the stent than the other side of the stent.

The invention may include any of the following aspects in various combinations and may also include any other aspect described below in the written description or in the attached drawings.

A method for making a stent-graft, comprising:
disposing a stent on a mandrel, the mandrel extending axially through an inner lumen of the stent and the stent being in contact with an outer circumference of the mandrel, wherein the stent is self-expanding to an expanded relaxed state, and a diameter of the outer circumference of the mandrel is at least 5% larger than a diameter of the expanded relaxed state of the stent, the stent thereby being circumferentially stretched by the mandrel;
adhering a graft layer to the stent while the stent is disposed on the mandrel; and
removing the stent from the mandrel after the graft layer is adhered to the stent, wherein the stent circumferentially contracts substantially to the expanded relaxed state, the graft layer thereby being at least partially wrinkled in the expanded relaxed state.

The method wherein the stent is laser cut from a metal cannula and comprises a series of zig-zag rings interconnected by longitudinal members.

The method wherein the graft layer comprises a substantially inelastic material.

The method wherein the graft layer comprises polyethylene terephthalate.

The method wherein the diameter of the outer circumference of the mandrel is 5% to 20% larger than the diameter of the expanded relaxed state of the stent.

The method wherein the diameter of the outer circumference of the mandrel is about 10% larger than the diameter of the expanded relaxed state of the stent.

The method wherein the graft layer is adhered to the stent by electrospinning polyethylene terephthalate dissolved in trifluoroacetic acid onto the stent.

The method wherein the graft layer is adhered to the stent by applying a first polyethylene terephthalate material having a first molecular weight to the stent and applying a second polyethylene terephthalate material having a second molecular weight over the first polyethylene terephthalate material, the first molecular weight being lower than the second molecular weight and a first melting temperature of the first polyethylene terephthalate material thereby being lower than a second melting temperature of the second polyethylene terephthalate material, and thereafter heating the stent, the first polyethylene terephthalate material, and the second polyethylene terephthalate material to a temperature between the first melting temperature and the second melting temperature.

The method wherein the first melting temperature is at least 10° C. lower than the second melting temperature.

The method wherein the graft layer comprises a substantially inelastic material, and the diameter of the outer circumference of the mandrel is 5% to 20% larger than the diameter of the expanded relaxed state of the stent.

The method wherein the graft layer is adhered to the stent by applying a first polyethylene terephthalate material having a first molecular weight to the stent and applying a second polyethylene terephthalate material having a second molecular weight over the first polyethylene terephthalate material, the first molecular weight being lower than the second molecular weight and a first melting temperature of the first polyethylene terephthalate material thereby being lower than a second melting temperature of the second polyethylene terephthalate material, and thereafter heating the stent, the first polyethylene terephthalate material, and the second polyethylene terephthalate material to a temperature between the first melting temperature and the second melting temperature.

The method wherein the first melting temperature is at least 10° C. lower than the second melting temperature, and the stent is laser cut from a metal cannula and comprises a series of zig-zag rings interconnected by longitudinal members.

The method wherein the graft layer comprises polyethylene terephthalate, the diameter of the outer circumference of the mandrel is about 10% larger than the diameter of the expanded relaxed state of the stent, and the graft layer is adhered to the stent by electrospinning polyethylene terephthalate dissolved in trifluoroacetic acid onto the stent.

The method wherein the stent is laser cut from a metal cannula and comprises a series of zig-zag rings interconnected by longitudinal members.

A method for making a stent-graft, comprising:
disposing a stent on a mandrel, the mandrel extending axially through an inner lumen of the stent, wherein the stent is self-expanding to an expanded relaxed state with a predetermined length at the expanded relaxed state, and the stent is axially stretched on the mandrel at least 10% more than the predetermined length;

adhering a graft layer to the stent while the stent is disposed and axially stretched on the mandrel; and removing the stent from the mandrel after the graft layer is adhered to the stent, wherein the stent axially contracts substantially to the predetermined length, the graft layer thereby being at least partially wrinkled in the expanded relaxed state.

The method wherein the stent is axially stretched on the mandrel 10% to 40% longer than the predetermined length.

The method wherein the stent is axially stretched on the mandrel with protrusions extending out from an outer circumference of the mandrel a distance less than a thickness of the stent, the protrusions being disposed adjacent opposing ends of the stent and extending radially partially through portions of the stent to stretch the stent on the mandrel.

A method for making a stent-graft, comprising:

disposing a stent on a mandrel, the mandrel extending axially through an inner lumen of the stent, wherein the stent is self-expanding to an expanded relaxed state with a predetermined length at the expanded relaxed state, and one side of the stent is axially stretched on the mandrel at least 10% more than an opposing side of the stent;

adhering a graft layer to the stent while the stent is disposed and axially stretched on the mandrel; and removing the stent from the mandrel after the graft layer is adhered to the stent, wherein the stent axially contracts substantially to the predetermined length, the graft layer thereby being at least partially wrinkled in the expanded relaxed state.

The method wherein the mandrel is straight.

The method wherein the mandrel is curved.

BRIEF DESCRIPTION OF SEVERAL VIEWS OF THE DRAWINGS

The invention may be more fully understood by reading the following description in conjunction with the drawings, in which.

DETAILED DESCRIPTION

Figure 1:
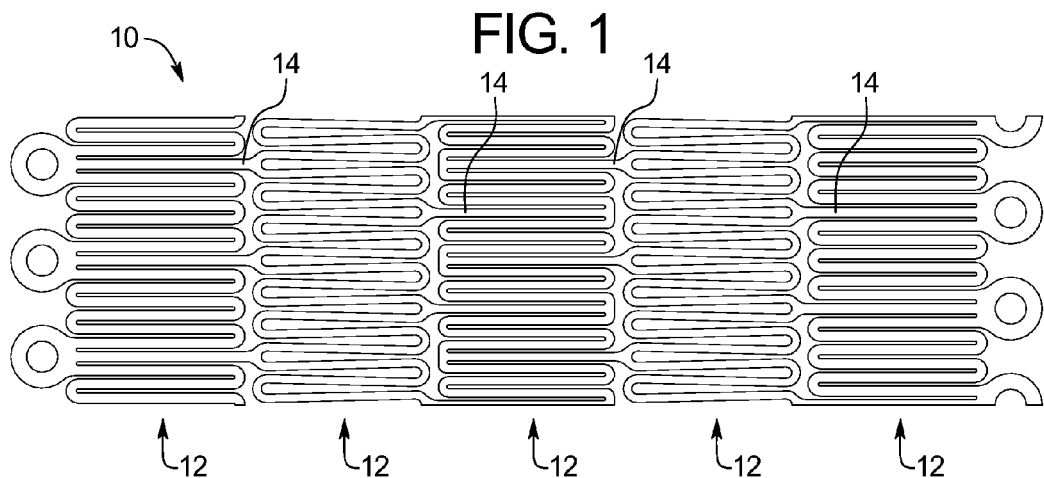
FIG. 1 is a laid out view of a stent.

Referring now to the figures, and particularly to FIG. 1, a stent 10 is shown in a laid out view for illustration purposes.

As one of ordinary skill will readily recognize, the stent 10 forms a cylindrical structure with the top and bottom edges shown in the figure connected to each other. Preferably, the stent 10 is made by laser cutting the structure of the stent 10 from a metal cannula made from nitinol or stainless steel. As shown FIG. 1, the stent 10 structure is preferably formed with a series of zig-zag rings 12 that are interconnected to each other by longitudinal members 14. However, there are many other types of stent structures that may also be used.

The stent 10 is preferably self-expanding so that it elastically expands to a relaxed expanded diameter. Thus, in order to deploy the stent-graft 16, the stent 10 may be forcibly compressed and retained in the compressed state with a retaining sheath or other mechanism. Once the stent-graft 16 is positioned at the desired treatment site, the stent 10 may be released so that it self-expands until the stent-graft 16 comes into contact with the surrounding body tissues.

Figure 2:
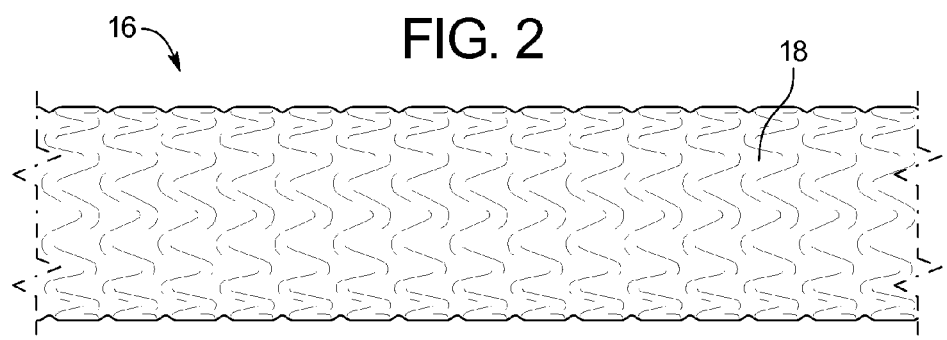
FIG. 2 is a side view of a stent-graft in a relaxed expanded state with wrinkles in the graft layer.

As shown in FIG. 2, the stent-graft 16 also includes a graft layer 18 that is adhered to the stent 10. The graft layer 18 may be any biocompatible graft material and may be either inelastic or elastic. An example of a substantially inelastic material includes polyethylene terephthelate, while examples of elastic materials include polyurethane and silicone. In addition, the graft layer 18 may also be biodegradable. Examples of biodegradable materials include polylactic acid and polyglycolic acid and copolymers thereof.

The graft layer 18 may be adhered to the stent 10 in a variety of ways. For example, the graft layer 18 may be adhered to the stent 10 by electrospinning the graft material onto the outer surface of the stent 10. This may be accomplished by dissolving polyethylene terephthelate in trifluoroacetic acid and electrospinning the mixture onto the stent 10. The graft layer 18 may also be adhered to the stent 10 by melt spinning or spraying the graft material on the stent 10. The graft layer 18 may also be adhered to the stent 10 by dip coating the graft material onto the stent 10 by positioning the stent 10 between a mandrel and a die and flowing the graft material into the annular space between the mandrel and the die. In yet another method of adhering the graft layer 18 to the stent 10, two different polyethylene terephthelate materials may be used with different molecular weights and different melting temperatures. The first polyethylene terephthelate material may be an amorphous polyethylene terephthelate dissolved in a solvent, such as trifluoroacetic acid and dichloromethane. The stent 10 may then be dipped into the solution. After the solvent has evaporated, fibers of the second polyethylene terephthelate material may be electrospun or otherwise wrapped over the first polyethylene terephthelate material. The first polyethylene terephthelate material preferably has a lower molecular weight than the second polyethylene terephthelate material and has a melting point that is at least 10° C. lower than the melting point of the second polyethylene terephthelate material. The stent 10 and first and second polyethylene terephthelate materials may then be heated to a temperature between the two melting points of the first and second polyethylene terephthelate materials. As a result, the first polyethylene terephthelate material will bond the second polyethylene terephthelate material to the stent 10. It is preferred that whichever method is used to adhere the graft layer 18 to the stent 10 that the graft layer 18 is adhered directly to the structure of the stent 10 and that sutures are not used to attach the graft layer 18 to the stent 10.

Figure 3:
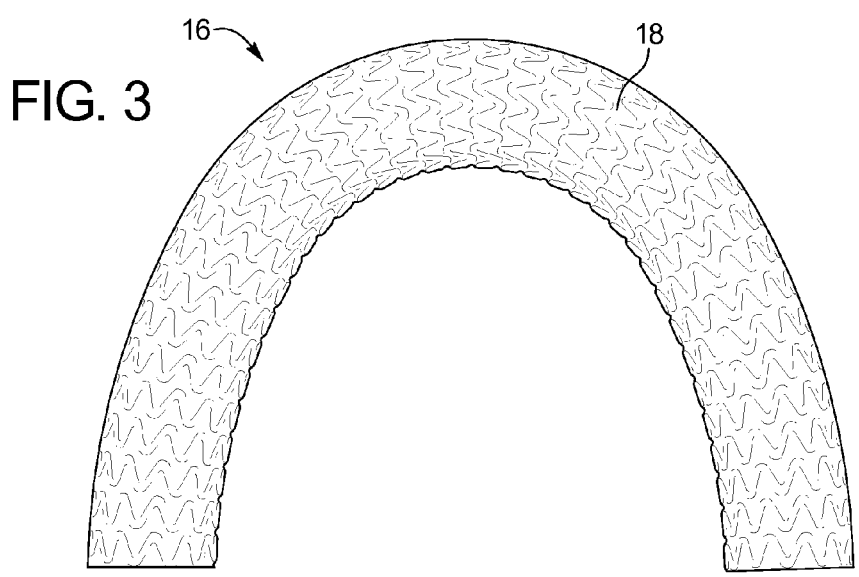
FIG. 3 is a side view of the stent-graft bent in a curve.

As shown in FIGS. 2 and 3, the graft layer 18 is at least partially wrinkled in the expanded relaxed state of the stent 10. This allows the stent-graft 16 to be more flexible. For example, as shown in FIG. 3, the stent-graft 16 may be bent more easily than a stent-graft without wrinkles in the expanded relaxed state. This may allow the stent-graft 16 to be axially stretched, twisted, bent and/or radially deformed to a greater degree without overstressing the graft layer 18, which could cause the graft material to fail.

Figure 4:
FIG. 4 is a schematic view of a stent mounted on a mandrel, showing the stent circumferentially stretched on the mandrel.

As shown in FIG. 4, the stent 10 may be mounted onto a mandrel 20 that extends axially through the inner lumen of the stent 10. The outer diameter of the mandrel 20 may be at least 5% larger than the diameter of the expanded relaxed state of the stent 10 so that the stent 10 contacts the outer circumference of the mandrel 20 and is circumferentially stretched by the mandrel 20. The graft layer 18 is then adhered to the stent 10 while it is mounted on the mandrel 20. After the graft layer 18 has been adhered to the stent 10, the stent 10 is removed from the mandrel 20. As a result, the stent 10 contracts circumferentially back to the expanded relaxed state of the stent 10. This causes the graft layer 18 to partially wrinkle when the stent-graft 16 is in the expanded relaxed state. It is preferable that the outer diameter of the mandrel 20 not be larger than 20% of the diameter of the expanded relaxed state of the stent 10, and it is more preferable that the outer diameter of the mandrel 20 be about 10% larger than the diameter of the expanded relaxed state of the stent 10.

Figure 5A:
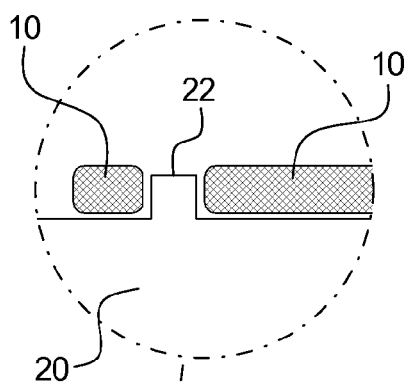
FIG. 5A is an expanded view of the mandrel and stent of FIG. 5, showing a protrusion extending partially through the stent.
Figure 5:
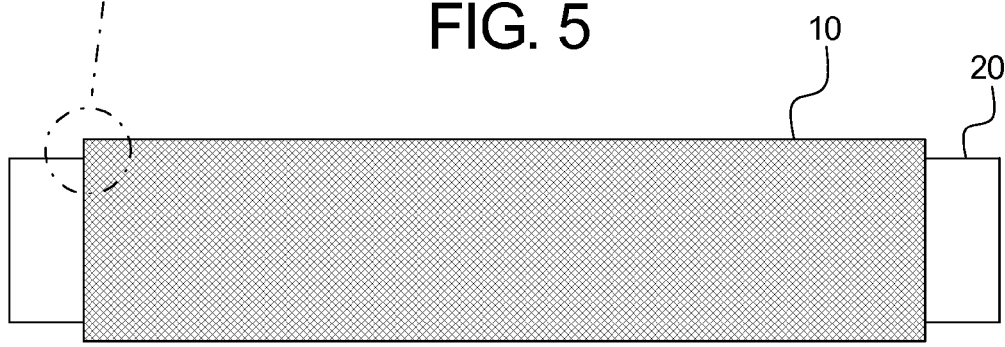
FIG. 5 is a schematic view of a stent mounted on a mandrel, showing the stent axially stretched on the mandrel.

As shown in FIG. 5, the stent 10 may also be mounted on a mandrel 20 to axially stretch the stent 10 compared to the predetermined length of the stent 10 when it is at its expanded relaxed state. For example, this may be accomplished as shown in FIG. 5A with a protrusion 22 that extends out from the outer circumference of the mandrel 20. Preferably, the protrusion 22 extends out less than the thickness of the stent 10 so that when the stent 10 is mounted on the mandrel 20, the protrusion 22 does not extend all the way through the wall of the stent 10. Thus, the protrusion 22 may extend only partially through a portion of the stent 10 to restrain the stent 10 axially along the mandrel 20. In addition, by extending only partially through the wall of the stent 10, the graft layer 18 is able to coat the stent 10 and cover the protrusion 22 without leaving an opening in the graft layer 18. Preferably, protrusions 22 are provided at least adjacent each of the opposing ends of the stent 10 in order to stretch the entire length of the stent 10. Preferably, the stent 10 is axially stretched on the mandrel 20 at least 10% farther than the predetermined length of the stent 10 in its expanded relaxed state, and it is more preferable that the stent 10 is not axially stretched more than 40% longer than the predetermined length of the stent 10. As a result, when the stent-graft 16 is removed from the mandrel 20, the stent 10 axially contracts back to its predetermined length at the expanded relaxed state. This also causes the graft layer 18 to partially wrinkle when the stent-graft 16 is in the expanded relaxed state.

Figure 6A:
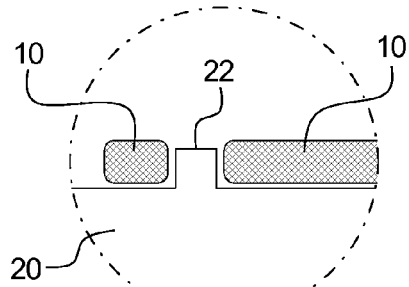
FIG. 6A is an expanded view of the mandrel and stent of FIG. 6, showing a protrusion extending partially through the stent.
Figure 6:
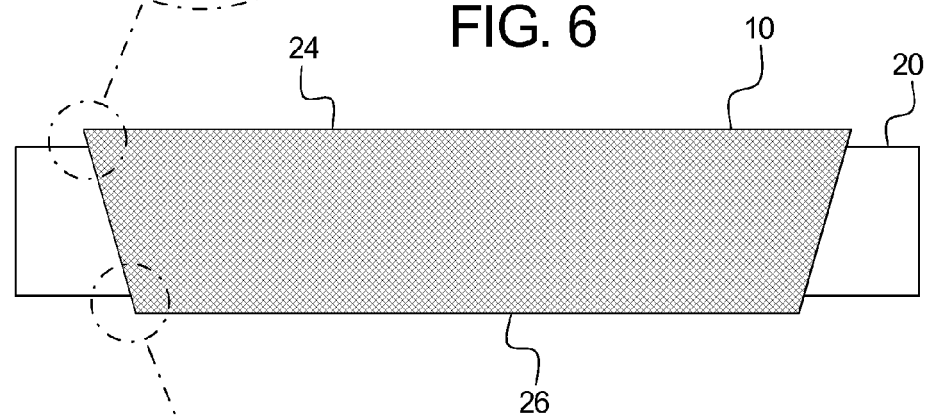
FIG. 6 is a schematic view of a stent mounted on a mandrel, showing one side of the stent axially stretched more than the other side of the stent on a straight mandrel.
Figure 6B:
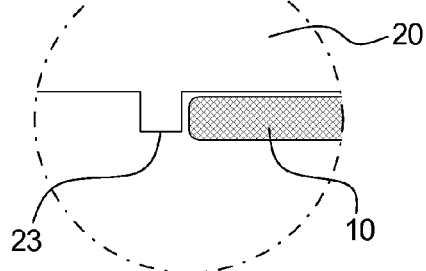
FIG. 6B is an expanded view of the mandrel and stent of FIG. 6, showing a protrusion extending adjacent an end portion of the stent.

As shown in FIG. 6, the stent 10 may also be mounted on a mandrel 20 to axially stretch one side 24 of the stent 10 more than the other side 26 of the stent 10. For example, as shown in FIG. 6A, this may be accomplished by using a protrusion 22 of the first side 24 of the stent 10 that extends partially through a portion of the stent 10. By using similar protrusions 22 at each end of the stent 10, the protrusions 22 may restrain the first side 24 in an axially stretched condition. As shown in FIG. 6B, a protrusion 23 may be used on the second side 26 to axially restrain the second side 26 from stretching the same amount as the first side 24. The protrusion 23 on the second side 26 may be located outside of the end of the stent 10 so that the protrusion 23 does not extend through the wall of the stent 10. A similar protrusion 23 may also be provided at the opposite end of the stent 10 to restrain both ends of the second side 26. Preferably, the stent 10 is axially stretched at least 10% more on the first side 24 of the stent 10 than on the second side 26 of the stent 10, and is preferably axially stretched no more than 40% more on the first side 24 than the second side 26 of the stent 10. As a result, when the stent-graft 16 is removed from the mandrel 20, the stent 10 axially contracts back to its predetermined length at the expanded relaxed state. This also causes the graft layer 18 to partially wrinkle more on the first side 24 than the second side 26 when the stent-graft 16 is in the expanded relaxed state.

Figure 7:
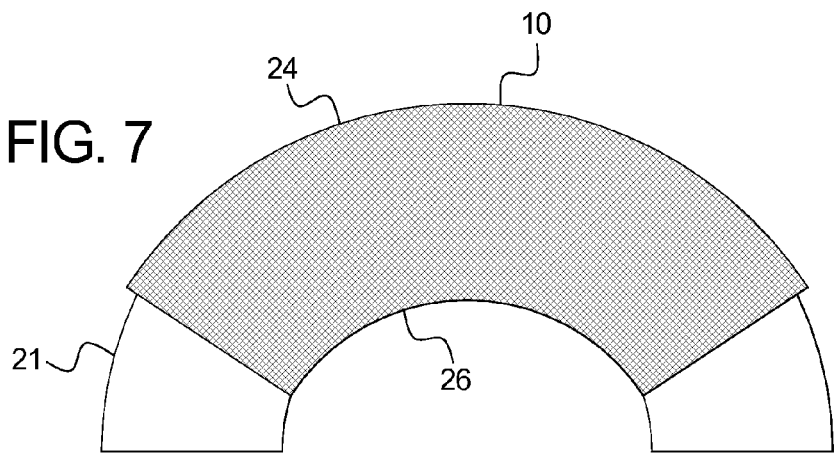
FIG. 7 is a schematic view of a stent mounted on a mandrel, showing one side of the stent axially stretched more than the other side of the stent on a curved mandrel.

As shown in FIG. 7, the stent 10 may also be axially stretched more on the first side 24 than the second side 26 by mounting the stent 10 on a curved mandrel 21. Thus, unlike FIG. 6 where the mandrel 20 is straight, the curved mandrel 21 of the FIG. 7 may not require protrusions 22, 23 to accomplish the increased stretch on the first side 24. However, protrusions may be used if desired. Like FIG. 6, it is preferred that the first side 24 is axially stretched at least 10% and not more than 40% more than the second side 26. As a result, when the stent-graft 16 is removed from the mandrel 23, the stent 10 axially contracts back to its predetermined length at the expanded relaxed state. This also causes the graft layer 18 to partially wrinkle more on the first side 24 than the second side 26 when the stent-graft 16 is in the expanded relaxed state.

While preferred embodiments of the invention have been described, it should be understood that the invention is not so limited, and modifications may be made without departing from the invention. The scope of the invention is defined by the appended claims, and all devices that come within the meaning of the claims, either literally or by equivalence, are intended to be embraced therein. Furthermore, the advantages described above are not necessarily the only advantages of the invention, and it is not necessarily expected that all of the described advantages will be achieved with every embodiment of the invention.

We claim:

1. A method for making a stent-graft, comprising:
    disposing a metal stent on a mandrel, said mandrel extending axially through an inner lumen of said metal stent and said metal stent being in contact with an outer circumference of said mandrel, wherein said metal stent is self-expanding to an expanded relaxed state, and a diameter of said outer circumference of said mandrel is at least 5% larger than a diameter of said expanded relaxed state of said metal stent, said metal stent thereby being circumferentially stretched by said mandrel;
    adhering a graft layer to said metal stent by applying a first polyethylene terephthalate material having a first molecular weight to said metal stent and applying a second polyethylene terephthalate material having a second molecular weight over said first polyethylene terephthalate material, said first molecular weight being lower than said second molecular weight and a first melting temperature of said first polyethylene terephthalate material thereby being lower than a second melting temperature of said second polyethylene terephthalate material, and thereafter heating said metal stent, said first polyethylene terephthalate material, and said second polyethylene terephthalate material to a temperature between said first melting temperature and said second melting temperature; and
    removing said metal stent from said mandrel after said graft layer is adhered to said metal stent, wherein said metal stent circumferentially contracts substantially to said expanded relaxed state, said graft layer thereby being at least partially wrinkled in said expanded relaxed state.

2. The method according to claim 1, wherein said metal stent is laser cut from a metal cannula and comprises a series of zig-zag rings interconnected by longitudinal members.

3. The method according to claim 1, wherein said graft layer comprises a substantially inelastic material.

4. The method according to claim 1, wherein said diameter of said outer circumference of said mandrel is 5% to 20% larger than said diameter of said expanded relaxed state of said metal stent.

5. The method according to claim 4, wherein said diameter of said outer circumference of said mandrel is about 10% larger than said diameter of said expanded relaxed state of said metal stent.

6. The method according to claim 1, wherein said second polyethylene terephthalate material is adhered to said metal stent by electrospinning polyethylene terephthalate dissolved in trifluoroacetic acid onto said metal stent.

7. The method according to claim 1, wherein said first melting temperature is at least 10° C. lower than said second melting temperature.

8. The method according to claim 1, wherein said graft layer comprises a substantially inelastic material, and said diameter of said outer circumference of said mandrel is 5% to 20% larger than said diameter of said expanded relaxed state of said metal stent.

9. The method according to claim 8, wherein said first melting temperature is at least 10° C. lower than said second melting temperature, and said metal stent is laser cut from a metal cannula and comprises a series of zig-zag rings interconnected by longitudinal members.

10. The method according to claim 1, wherein said diameter of said outer circumference of said mandrel is about 10% larger than said diameter of said expanded relaxed state of said metal stent, and said graft layer is adhered to said metal stent by electrospinning polyethylene terephthalate dissolved in trifluoroacetic acid onto said metal stent.

11. The method according to claim 10, wherein said metal stent is laser cut from a metal cannula and comprises a series of zig-zag rings interconnected by longitudinal members.

12. The method according to claim 1, wherein said first polyethylene terephthalate material is adhered to said metal stent by dipping said metal stent in a polyethylene terephthalate solution.

13. The method according to claim 12, wherein said second polyethylene terephthalate material is adhered to said first polyethylene terephthalate material by electrospinning polyethylene terephthalate dissolved in trifluoroacetic acid onto said first polyethylene terephthalate material.

14. The method according to claim 13, wherein said second polyethylene terephthalate material is adhered to said metal stent by melting said first polyethylene terephthalate material thereby bonding said second polyethylene terephthalate and said metal stent.

15. The method according to claim 14, wherein no sutures are used to attach said graft layer to said metal stent.

* * * * *